(12) United States Patent
Park et al.

(10) Patent No.: US 10,185,808 B2
(45) Date of Patent: Jan. 22, 2019

(54) APPARATUS AND METHOD FOR DIAGNOSIS

(71) Applicant: Samsung Electronics Co., Ltd., Suwon-si, Gyeonggi-do (KR)

(72) Inventors: Jin-Man Park, Yongin-si (KR); Kyoung-Gu Woo, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/591,776

(22) Filed: May 10, 2017

(65) Prior Publication Data

US 2017/0262600 A1 Sep. 14, 2017

Related U.S. Application Data

(63) Continuation of application No. 14/057,470, filed on Oct. 18, 2013, now Pat. No. 9,684,769.

(30) Foreign Application Priority Data

Nov. 16, 2012 (KR) .......................... 10-2012-0130480

(51) Int. Cl.
  *G06T 7/00* (2017.01)
  *G06F 19/00* (2018.01)
  *G16H 50/20* (2018.01)

(52) U.S. Cl.
  CPC .......... *G06F 19/345* (2013.01); *G06T 7/0012* (2013.01); *G16H 50/20* (2018.01); *G06T 2207/30068* (2013.01); *G06T 2207/30096* (2013.01)

(58) Field of Classification Search
  CPC ......... G06T 7/0012; G06T 2207/30068; G06T 2207/30069
  See application file for complete search history.

(56) References Cited

U.S. PATENT DOCUMENTS

| 5,986,662 | A | 11/1999 | Argiro et al. |
| 5,987,345 | A | 11/1999 | Engelmann et al. |
| 6,901,156 | B2 | 5/2005 | Giger et al. |

(Continued)

FOREIGN PATENT DOCUMENTS

| CN | 1650312 A | 8/2005 |
| CN | 1959687 A | 5/2007 |

(Continued)

OTHER PUBLICATIONS

Chinese Office Action dated Sep. 5, 2018, issued in SIPO in connection with a Chinese application No. 201310574527.0.

(Continued)

*Primary Examiner* — Kim Vu
*Assistant Examiner* — Molly Delaney
(74) *Attorney, Agent, or Firm* — Jefferson IP Law, LLP

(57) ABSTRACT

There are provided an apparatus and method for diagnosis using a medical image. The apparatus includes: an analyzing unit configured to detect a lesion area, and generate a group of candidate lesion areas with respect to the detected lesion area; and an interface unit configured to arrange one or more candidate lesion areas selected among the group of candidate lesion areas with information about each of the one or more selected candidate lesion areas in a first region of an interface.

20 Claims, 5 Drawing Sheets

(56) References Cited

U.S. PATENT DOCUMENTS

| | | |
|---|---|---|
| 7,308,126 B2 | 12/2007 | Rogers et al. |
| 7,418,119 B2 | 8/2008 | Leichter et al. |
| 7,593,562 B2 | 9/2009 | Harrington et al. |
| 7,783,094 B2 | 8/2010 | Collins et al. |
| 8,073,214 B2 | 12/2011 | Hong et al. |
| 8,185,511 B2 | 5/2012 | Agnihorti et al. |
| 8,391,574 B2 | 3/2013 | Collins et al. |
| 8,480,583 B2 | 7/2013 | Lundberg |
| 8,799,013 B2 | 8/2014 | Gustafson |
| 2002/0131625 A1 | 9/2002 | Vining et al. |
| 2004/0002874 A1 | 1/2004 | Shaffer et al. |
| 2004/0008876 A1 | 1/2004 | Lure et al. |
| 2006/0064396 A1 | 3/2006 | Wei et al. |
| 2006/0094954 A1 | 5/2006 | Fan et al. |
| 2006/0120608 A1 | 6/2006 | Luo et al. |
| 2006/0146071 A1 | 7/2006 | Morita et al. |
| 2006/0274928 A1* | 12/2006 | Collins .............. A61B 6/00 382/132 |
| 2007/0003119 A1 | 1/2007 | Roehrig et al. |
| 2007/0003124 A1 | 1/2007 | Wood et al. |
| 2007/0063998 A1 | 3/2007 | Mahesh |
| 2007/0133852 A1 | 6/2007 | Collins et al. |
| 2008/0298766 A1 | 12/2008 | Wen et al. |
| 2009/0222286 A1 | 9/2009 | Elsholz |
| 2009/0309874 A1 | 12/2009 | Salganicoff et al. |
| 2009/0327890 A1 | 12/2009 | Mertz et al. |
| 2010/0021031 A1* | 1/2010 | Brockway ............ G06K 9/3233 382/128 |
| 2011/0137132 A1 | 6/2011 | Gustafson |
| 2011/0144482 A1 | 6/2011 | Sendai et al. |
| 2011/0273589 A1 | 11/2011 | Mochimizo |
| 2012/0166211 A1 | 6/2012 | Park et al. |
| 2013/0152020 A1* | 6/2013 | Nishiyama ......... A61B 1/00009 715/835 |

FOREIGN PATENT DOCUMENTS

| | | |
|---|---|---|
| CN | 101061513 A | 10/2007 |
| CN | 101076724 A | 11/2007 |
| KR | 10-2008-0021723 A | 3/2008 |
| KR | 10-2009-0010555 A | 1/2009 |
| KR | 10-2009-0019837 A | 2/2009 |
| KR | 10-2010-0051477 A | 5/2010 |
| WO | 2006/128302 A1 | 12/2006 |

OTHER PUBLICATIONS

European Preliminary Opinion dated Oct. 18, 2018, issued in a counterpart European application No. 13192990.3.

Europeon Patent Office; European Preliminary Opinion dated Nov. 22, 2018, issued in a counterpart European application No. 13192990.3-1210; Nov. 22, 2018; pp. 1-16.

* cited by examiner

APPARATUS AND METHOD FOR DIAGNOSIS

CROSS-REFERENCE TO RELATED APPLICATION(S)

This application is a continuation application of prior application Ser. No. 14/057,470, filed on Oct. 18, 2013, and claimed the benefit under 35 U.S.C. § 119(a) of Korean Patent Application No. 10-2012-0130480, filed on Nov. 16, 2012, the entire disclosure of which is incorporated herein by reference for all purposes.

BACKGROUND

Field

The following description relates to an apparatus and a method for diagnosis, and to an apparatus and a method that support computer-aided diagnosis (CAD) through medical image analysis.

Description of Related Art

Computer-aided diagnosis (CAD) is a technology used in medicine that assists doctors in interpreting medical images by detecting a suspected abnormal region in a medical image, and analyzing the region to provide an initial diagnosis of a lesion. Thus, highly-accurate diagnoses are required to help a user, such as a radiologist, in making a final diagnosis. However, an automatic diagnosis algorithm used in a CAD system does not result in a 100% accuracy for its diagnostic result. Thus, the user has to analyze and modify the diagnosis performed by a CAD system. For the user to analyzing the diagnostic result of a CAD system, the user needs to evaluate various images of the abnormal region from different angles. However, there are restrictions in time and space when such an evaluation is carried out. Thus, it is hard to analyze and modify a diagnostic result provided by a CAD system through a user interface provided in such a CAD system.

SUMMARY

In one general aspect, there is provided an apparatus, including: an analyzing unit configured to detect a lesion area, and generate a group of candidate lesion areas with respect to the detected lesion area; and an interface unit configured to arrange one or more candidate lesion areas selected among the group of candidate lesion areas with information about each of the one or more selected candidate lesion areas in a first region of an interface.

The interface unit may be configured to arrange the one or more selected candidate lesion areas based on priority information, class information, or a combination of the priority information and the class information.

The interface unit may be configured to arrange a candidate lesion area having a higher priority closer to a center of the first region of the interface in comparison to another candidate lesion area having a lower priority.

The interface unit may be configured to display the one or more selected candidate lesion areas in the first region with different sizes based on the priority information.

The interface unit may be configured to arrange the one or more selected candidate lesion areas in the first region based on the class information.

The interface unit may configured to display the one or more selected candidate lesion areas with boundaries or frames of different color in the first region based on the class information.

The general aspect of the apparatus may further include: a processing unit configured to calculate priorities of each candidate lesion areas in the group of candidate lesion areas, and select the one or more candidate lesion areas to be arranged from the group of candidate lesion areas based on the priorities.

The processing unit may be configured to calculate the priorities based on a probability of a user selecting a candidate lesion area from among the group of candidate lesion areas.

In response to a user selecting one of the candidate lesion areas arranged in the first region, the interface unit may be configured to display detailed information about the selected candidate lesion area in a second region of the interface.

The detailed information may include feature information, class information, diagnostic result information or a combination thereof.

The interface unit may be configured to display in the second region one or more feature categories, selected based on priorities among feature categories relating to the selected candidate lesion area, and one or more feature selected based on priorities among features corresponding to each of the one or more feature categories.

In response to a user selecting one of the one or more feature categories displayed on the second region, the interface unit may be configured to display one or more features selected based on priorities among features corresponding to the selected feature category.

The analyzing unit may be configured to detect the lesion area by analyzing a medical image and to generate the group of candidate lesion areas by performing segmentation on the detected lesion area, and the interface may be displayed on a display unit.

In another general aspect, there is provided a method, the method involving: detecting a lesion area; generating a group of candidate lesion areas with respect to the detected lesion area; and arranging one or more candidate lesion areas selected among the group of candidate lesion areas and information about each of the one or more selected candidate lesion areas in a first region of an interface.

The arranging of the one or more selected candidate areas may involve arranging the one or more selected candidate areas based on priority information, class information, or a combination of the priority information and the class information.

The arranging of the one or more selected candidate lesion areas may involve arranging a candidate lesion area having a higher priority to be closer to a center of the first region in comparison to another candidate lesion area having a lower priority.

The arranging of the one or more selected candidate lesion areas in the first region may involve arranging the one or more candidate lesion areas in the first region in different sizes based on the priority information among the one or more selected candidate lesion areas.

The arranging of the one or more selected candidate lesion areas in the first region may involve arranging a position of the one or more selected candidate lesion areas in the first region based on the class information.

The arranging of the one or more selected candidate lesion areas in the first region may involve arranging the one or more selected candidate lesion areas in the first region with boundaries or frames of different color based on the class information.

The general aspect of the method may further involve: calculating priorities relative to each candidate lesion areas of the group of candidate lesion areas and selecting the one or more candidate lesion areas to be arranged from among the group of candidate lesion areas according to the calculated priorities.

The calculating of the priorities may involve determining a probability of a user selecting a candidate lesion area from among the group of candidate lesion areas.

The general aspect of the method may further involve: in response to a user selecting one of the one or more selected candidate lesion areas arranged in the first region, displaying detailed information about the selected candidate lesion area in a second region of the interface.

The detailed information may include feature information, class information, diagnostic result information, or a combination thereof.

The displaying of the detailed information in the second region may involve displaying one or more feature categories selected based on priorities among the one or more feature categories relating to the selected candidate lesion area, and one or more feature selected based on priorities among features corresponding each of the one or more feature categories.

The general aspect of the method may further involve: in response to a user selecting one of the one or more feature categories displayed on the second region, displaying one or more features selected based on priorities among features corresponding to the selected feature category.

The detecting of the lesion area may involve analyzing a medical image. The generating of the group of candidate lesion areas may involve performing segmentation on the detected lesion area. The arranging of the one or more candidate lesion areas may involve arranging the one or more selected candidate lesion areas in that interface that is displayed on a display unit.

Other features and aspects will be apparent from the following detailed description, the drawings, and the claims.

Figure 1:
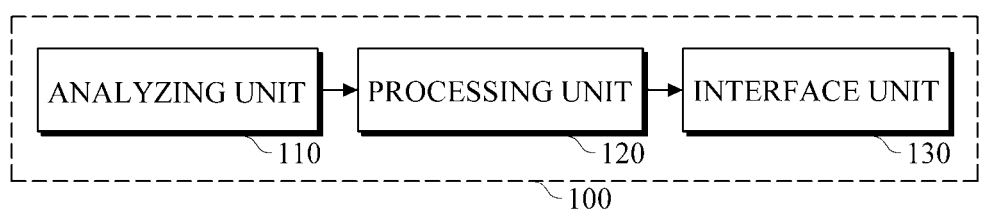
FIG. 1 is a block diagram illustrating an example of an apparatus for diagnosis.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will suggest themselves to those of ordinary skill in the art. Also, descriptions of well-known functions and constructions may be omitted for increased clarity and conciseness.

FIG. 1 is a block diagram illustrating an example of an apparatus for diagnosis. The apparatus for diagnosis may support a computer-aided diagnosis. Referring to FIG. 1, the apparatus 100 for diagnosis includes an analyzing unit 100, a processing unit 120 and an interface unit 130.

The analyzing unit 110 detects a lesion area from a medical image by analyzing the medical image. The detected lesion area is hereafter referred to as an original lesion area. With respected to the detected original lesion area, the analyzing unit 110 generates a group of candidate lesion areas. Using various lesion area detecting algorithms, the analyzing unit 110 may detect an original lesion area from a medical image. The medical image may be an image acquired through an ultrasonography, a Magnetic Resonance Imaging (MRI) device, a Computed Tomograpy (CT) device or other medical devices. The lesion-area detecting algorithms that may be used are not limited to the algorithms listed above, but include every well-known algorithm suitable for detecting the lesion area. After an original lesion area is detected, the analyzing unit 110 generates a group of candidate lesion areas, which is a plurality of candidate lesion areas. The analyzing unit 110 may generate the group of candidate lesion areas by performing image segmentation on the original lesion area into various separate regions, for example.

The analyzing unit 110 may generate detailed analytical information on each candidate lesion area of the plurality of candidate lesion areas. The detailed analytical information may include at least one of feature information, class information and diagnostic result information. The feature information may include one or more feature categories, and one or more features corresponding to each feature category. For example, the feature information may include feature categories of shape, margin, echo pattern, orientation and boundary, and the feature category of "shape" may include features of an irregular shape, a round shape and an oval shape. The diagnostic result information may indicate a result of a determination as to whether a corresponding candidate lesion area is benign or malignant based on the feature information. The class information refers to a class level determined according to a degree of benignancy or malignancy of a corresponding candidate lesion area. For example, the class level may relate to Breast Imaging-Reporting and Data System (BI-RADS).

The analyzing unit 110 may extract feature information about each candidate lesion area included in the group of candidate lesion areas, and generate class information and diagnostic result information based on the extracted feature information. The analyzing unit 110 may generate the diagnostic result information indicating whether a candidate lesion area is benign or malignant, using Discriminatively Trained Part Based Models (DPM), RegionGrowth or other analysis algorithms.

The processing unit 120 may select one or more candidate lesion areas from among the group of candidate lesion areas generated by the analyzing unit 110. For example, the processing unit 120 may calculate priorities relative to each candidate lesion area in the group of candidate lesion areas according to a predetermined criterion, and select one or more candidate lesion areas according to the calculated priority.

The predetermined criterion may be based on a probability of a user selecting a candidate lesion area from among the group of candidate lesion area, based on an analysis of user selections in the past. For example, if a candidate lesion area is most often selected by users as the most similar lesion area to an original lesion area when a final diagnosis is made, the corresponding candidate lesion area is determined to have the highest priority. According to an example, learning data is generated in advance based on users' selection of various lesion areas in the past. Then, the priorities relative to the group of candidate lesion areas may be calculated using a supervised learning algorithm that has been acquired using the learning data. For instance, the supervised learning algorithm may include Support Vector Machine (SVM) and Naïve Bayes Classification (NBC).

The interface unit 130 may arrange one or more candidate lesion areas, which are selected by the processing unit 120, and brief analytical information thereof in an interface according to a predetermined criterion. The interface unit 130 may display the interface on a display unit.

Figure 2:
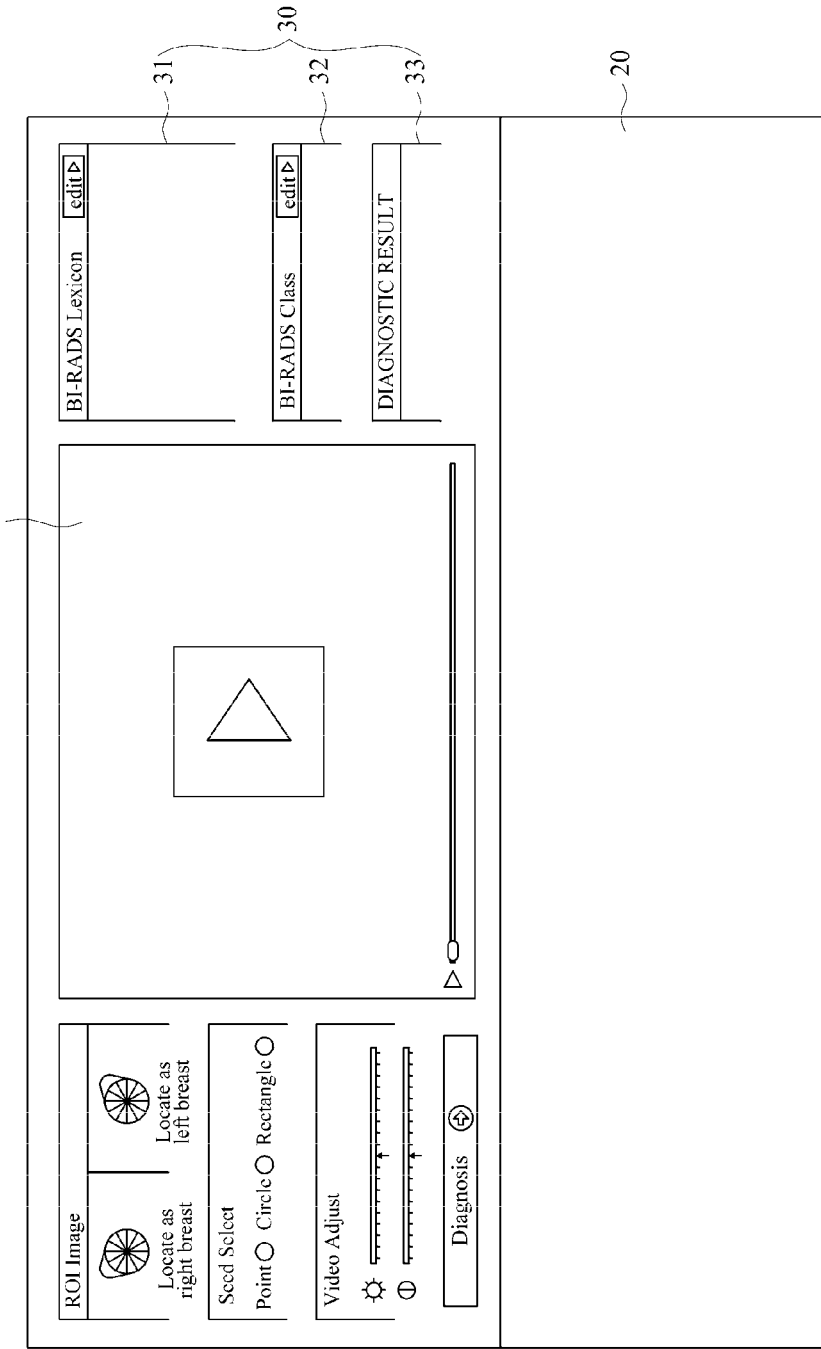
FIG. 2 is an example of an interface provided by an apparatus for diagnosis.
Figure 3:
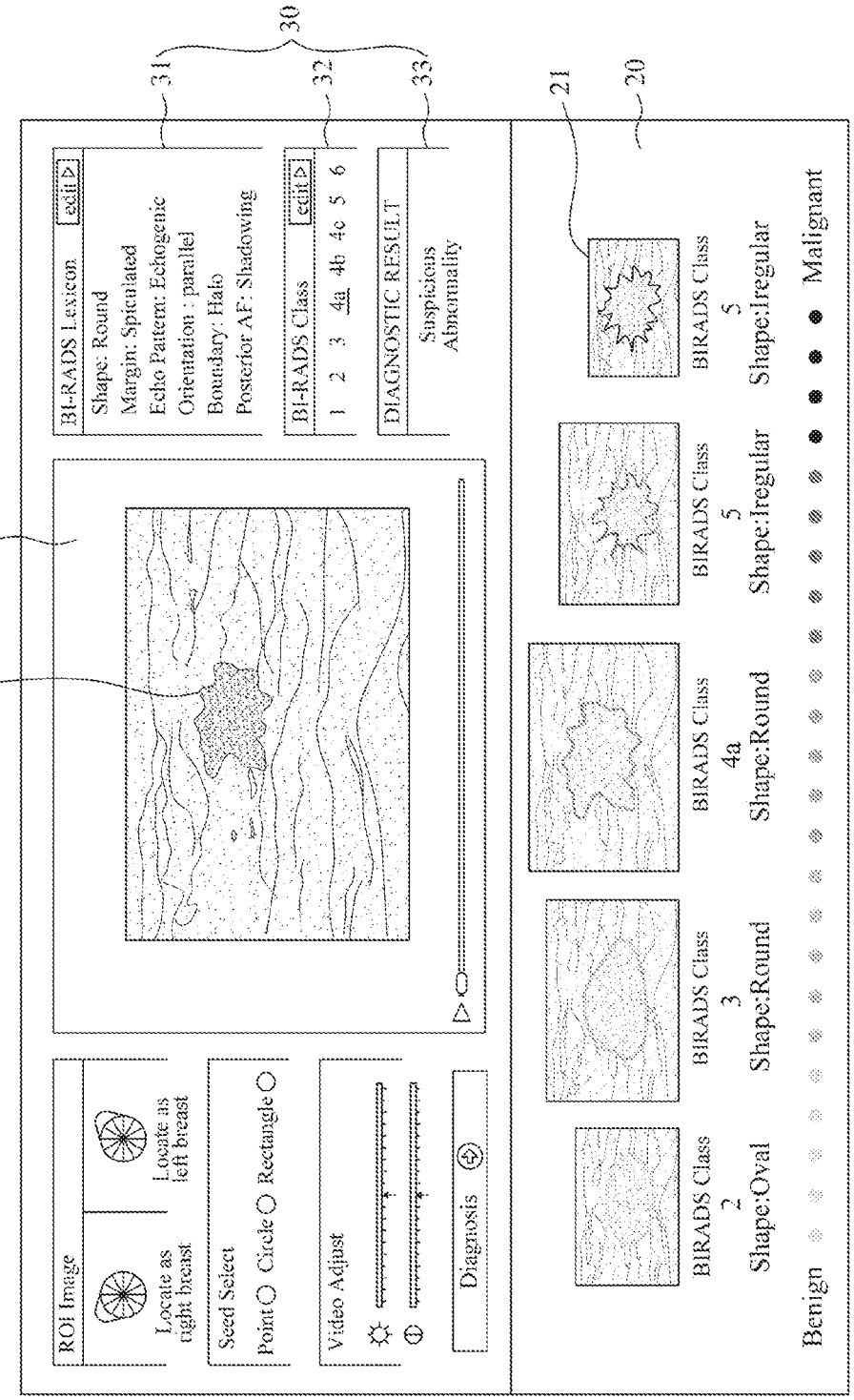
FIG. 3 is an example of an interface in which candidate lesion areas are displayed.
Figure 4:
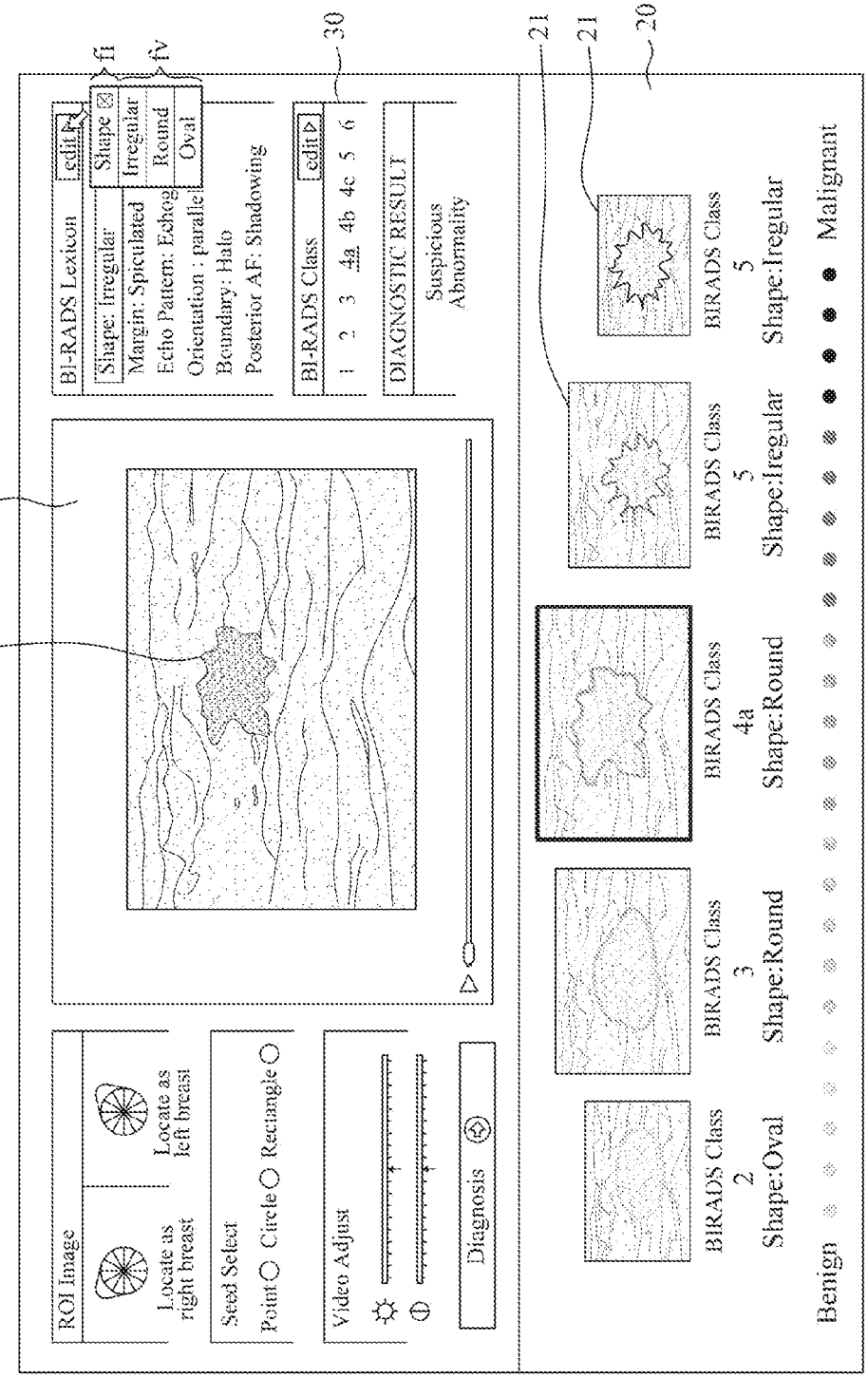
FIG. 4 is an example of an interface in which a feature illustrated in the interface of FIG. 3 is modified.

FIG. 2 is an example of an interface of an apparatus 100. FIG. 3 is an example of an interface illustrated in FIG. 2 in which candidate lesion areas are displayed. FIG. 4 is an example of an interface illustrated in FIG. 3 in which a feature of the interface of FIG. 3 is modified while candidate lesion areas are displayed.

Referring to FIGS. 1 to 4, an example of an interface 10 of an apparatus 100 may include a first region 20, a second region 30 and third region 40. In the first region 20, candidate lesion areas and brief analytical information regarding each of the candidate lesion areas are displayed. In the second region 30, detailed analytical information about one of the candidate lesion areas displayed on the first region 20 is displayed. The second region 30 may include a sub-region 31 in which feature information is displayed, a sub-region 32 in which class information is displayed, and a sub-region 33 in which diagnostic result information is displayed. In the third region 40, an original lesion area is displayed. Each of the regions mentioned above may have a fixed position in the interface 10, or the regions may be arranged differently according to a preference of a user for the convenience of the user. In addition, a user may change the position of each of the regions mentioned above. The interface 10 may be displayed on a display unit, such as a liquid crystal display (LCD), a light-emitting diode (LED) display, a plasma display panel (PDP), a touch screen, a projector, a screen, a terminal, and the like. A screen may be a physical structure that includes one or more hardware components that provide the ability to render a user interface and/or receive user input. The screen can encompass any combination of display region, a touch sensitive display, and/or a configurable area. The screen can be embedded in the hardware or may be an external peripheral device that may be attached and detached from the apparatus. The display unit may be a single-screen or a multi-screen display unit.

The interface unit 130 may arrange candidate lesion areas and brief analytical information thereof in the first region 20 of the interface 10 according to a predetermined criterion, and arrange an original lesion area 41 detected by the analyzing unit 110 in the third region 40 of the interface 10, as illustrated in FIG. 3. In the example illustrated in FIG. 3, five candidate lesion areas 21 are arranged in the upper part of the first region 20, and brief analytical information thereof are provided under each of the five candidate lesion areas 21. However, the number of candidate lesion areas displayed in the interface unit 130 is not limited to this example. Further, the number of displayed candidate lesion areas may vary depending on an analysis result of the original lesion area. Also, in one example, the brief analysis information displayed with the candidate lesion areas 21 may include at least one of class information and feature information relating to each of the five candidate lesion areas.

In this example, the predetermined criterion may include at least one of priority information calculated by the processing unit 120 with respect to the candidate lesion areas, the class information contained in the brief analytical information generated by the analyzing unit 110 with respect to each of the candidate lesion areas, and a combination of the priority information and the class information.

In an example, the interface unit 130 may arrange a candidate lesion area 21 having the highest priority at the center of the first region 20 based on priorities among candidate lesion areas 21. In addition, the interface unit 130 may arrange other candidate lesion areas 21 by alternating between the left side and the right side of the high priority candidate lesion area positioned in the center in descending order of priorities.

Referring to the example illustrated in FIG. 3, a class-4a candidate lesion area that is positioned at the center of the first region 20 has the highest priority. A class-3 candidate lesion area that is positioned to the left of the class-4a candidate lesion area has the second-highest priority. A class-5 candidate lesion area that is positioned to the right of the class-4a candidate lesion area has the third-highest priority. A class-2 candidate lesion area that is positioned to the far-left of the class-4a candidate lesion area has the fourth-highest priority. A class-5 candidate lesion area that is positioned to the far-right of the class-4a candidate lesion area has the lowest priority.

In another example, the interface unit 130 may arrange candidate lesion areas 21 in the first region 20 with different sizes or with different frame sizes, based on priorities among the candidate lesion areas. In the example illustrated in FIG. 3, the class-4a candidate lesion area having the highest priority is displayed inside the frame that has the largest size, and other candidate lesion areas are placed on the left side and right side of the class-4a candidate lesion area inside frames that have frame sizes that are reduced sequentially in descending order of the priorities.

In another example, based on priorities among candidate lesion areas, the interface unit 130 may use one or more colors for boundaries of the candidate lesion areas or for frames where the candidate lesion areas and brief analytical information thereof are to be displayed. For example, the interface unit 130 may use an easily noticeable color for a candidate lesion area 21 that has a higher priority, the priority corresponding to a possibility of a user selecting the candidate lesion area. The interface unit 130 may use a less noticeable color for a candidate lesion area 21 having a low priority. For example, an easily noticeable color includes red and yellow, while a less noticeable color includes green or gray. Alternatively, the boundaries or frames of candidate lesion areas may be displayed using the same color with different degrees of darkness.

In another example, the interface unit 130 may arrange candidate lesion areas 21 based on class information thereof in the first region, as illustrated in FIG. 3, In another example, the class-4a candidate lesion area having the highest priority may be arranged at the center of the first region, and candidate lesion areas whose class levels are lower than class 4a may be arranged on the left side of the class-4a candidate lesion area, while candidate lesion areas 21 whose class levels are higher than class 4a are arranged on the right side of the class-4a candidate lesion area. Meanwhile, in the event that two or more candidate lesion areas 21 have the same class level, a candidate lesion area 21 having a higher priority may be arranged closer to the center of the first region than other candidate lesion areas 21 having a relatively lower priority. In the example illustrated in FIG. 3, a class-5 candidate lesion area that is arranged closer to the center of the first region has a higher priority than that of the other class-5 candidate lesion area.

In another example, according to class levels of candidate lesion areas, the interface unit 130 may use one or more colors for boundaries of the candidate lesion areas 21 or for frames in which the candidate lesion areas and brief analytical information are to be displayed. For example, the interface unit 130 may use green for a candidate lesion area having a low class level because the lower a class level is more likely to correspond to a diagnosis of being benign, while red may be used for a candidate lesion area having a higher class level because the higher a class level is more likely to correspond to a diagnosis of being malignant. In another example, the boundaries and frames may be displayed using the same color with different degree of darkness.

As such, candidate lesion areas are arranged in an interface according to various criteria, thereby enabling a user to select an appropriate candidate lesion area more conveniently and more easily. However, the examples described above provided are merely as examples, and candidate lesion areas may be arranged according to other criterions.

As illustrated in FIG. 4, if a user selects one of candidate lesion areas 21 displayed on the first region 20, the interface unit 130 may display detailed analytical information about the selected candidate lesion area 21 in the second region 30. The detailed analytical information displayed on the second region 30 may include at least one of feature information, class information and diagnostic result information. In this example, the feature information displayed on the second region 30 may include at least some feature categories selected from among one or more feature categories that are extracted by the analyzing unit 110 with respect to the selected candidate lesion area 21, and at least one feature selected from among one or more features corresponding to each of the at least some feature categories.

According to a predetermined criterion, the processing unit 120 may calculate priorities among the candidate lesion areas based on the feature information extracted with respect to each of the candidate lesion areas. For example, the processing unit 120 may calculate priorities among one or more feature categories and priorities among one or more features corresponding to each of the one or more feature categories. The predetermined criterion may include, for example, a probability of a user selecting a feature category from among the one or more feature categories and a probability of a user selecting a feature from among features corresponding to each of the one or more feature categories. In response to the user selecting one of the candidate lesion areas 21 through the interface 10, the processing unit 120 may determine at least some feature categories and at least one feature corresponding to each of the at least some feature categories to thereby display in the interface 10, based on the priorities among feature categories and the priorities among features corresponding to a feature category.

In the example illustrated in FIG. 4, six feature categories are arranged in the second region 30 sequentially in a top to bottom order based on priorities among the feature categories. In this example, the feature categories that are to be displayed are determined by the interface unit 130. The features categories displayed in this example include shape, margin, echo pattern, orientation, boundary and posterior AF, as determined by the interface unit 130.

In addition, a feature having the highest priority among various features corresponding to each of the six categories is arranged next to a corresponding feature category. For instance, features with high priority are irregular, speculated, echogenic, parallel, halo and shadowing, for the example illustrated in FIG. 4. In the example illustrated in FIG. 4, class information, such as class 4a, is displayed on the central part of the second region 30, and diagnostic result information, such as suspicious abnormality, is displayed on the lower part of the second region 30.

In FIG. 4, the class information and the diagnostic result information are displayed on different frames. In this example, the diagnosis result displayed on the bottom part of the second region 30 corresponds to "suspicious abnormality." The class information includes a class level determined based on BI-RADS, which is displayed above the diagnosis result. However, in another example, the class information and the diagnostic result information may be displayed on the same frame, simultaneously.

Through the interface 10, a user is able to modify at least one of the feature information, the class information and the diagnostic result information displayed on the second region 30 of the interface 10. In the event that the user selects one of feature categories displayed on the second region 30 of the interface 10 to modify a corresponding feature, at least some features among features corresponding to the selected feature category may be provided to the user.

Referring to FIG. 4, in response to a user selecting a feature category, the processing unit 120 may determine features having the top three highest priorities to be displayed, based on priorities among features corresponding to the feature category. In FIG. 4, the user selects a feature category corresponding to "shape," the processing unit 120 determines features having the top three highest priorities, which happened to be "irregular," "round" and "oval" based on priorities among features corresponding to the feature category. Next, the interface unit 130 displays the selected feature category, such as "shape," in an upper part fi of a predetermined region of the interface 10, and the three features are displayed on the lower part fv of the predetermined region of the interface 10 sequentially based on the priorities among the three features. At this time, the interface unit 130 may display the features on a pop-up window in the surroundings of the selected feature category.

If a user modifies a feature by selecting a feature from among the features displayed in the interface 10, the processing unit 120 may receive the selected feature and store the received feature as a final diagnostic result.

Figure 5:
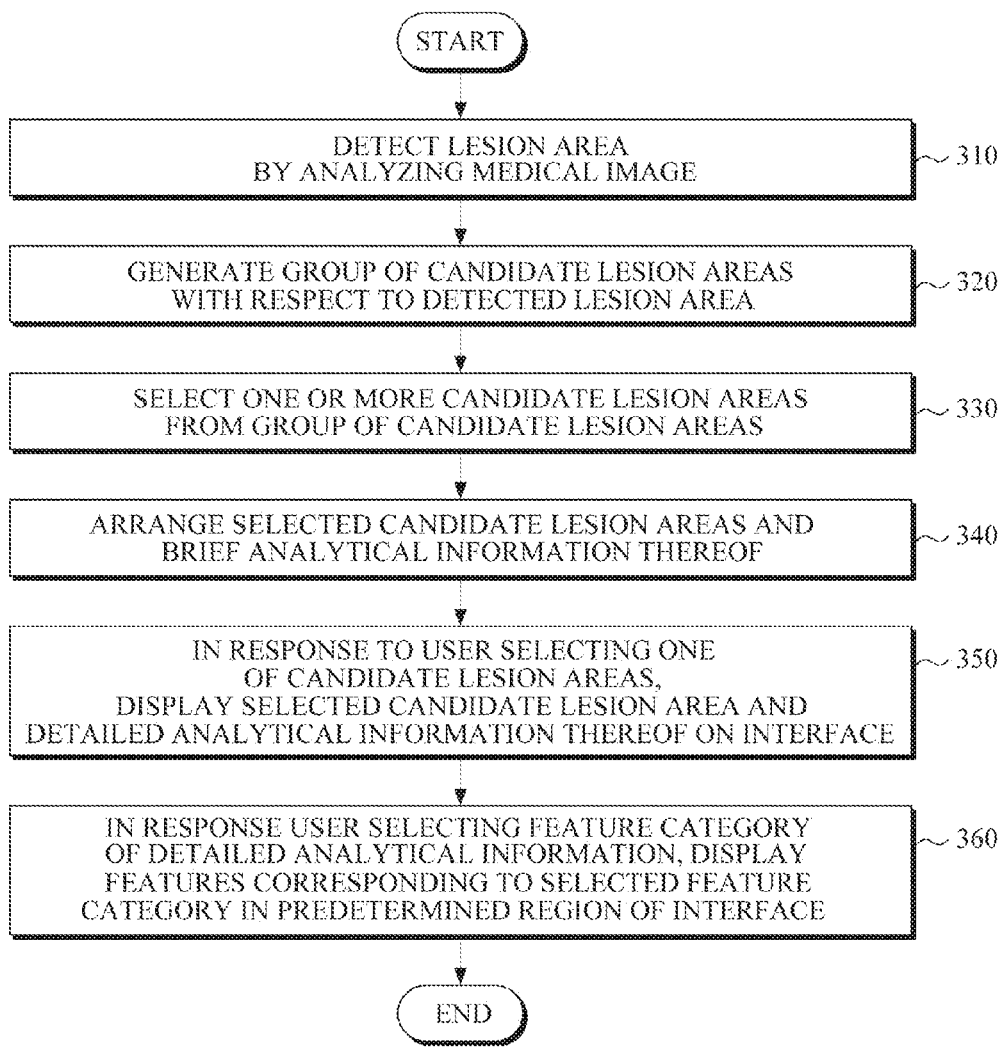
FIG. 5 is a flow chart illustrating an example of a method for diagnosis.

FIG. 5 is a flow chart illustrating an example of a method of diagnosis. The method may facilitate making a final diagnosis of a lesion by performing a computer-aided diagnosis (CAD), and outputting the result thereof to a user with various candidate lesion areas. With reference to FIG. 5, a method of using an apparatus 100 is also described.

The apparatus 100 detects a lesion area by analyzing a medical image in 310. In this example, a lesion area refers to a body part depicted in the medical image that is suspected of being abnormal. For example, the medical image may depict tissues or cell masses that are suspected of being abnormal.

Once an original lesion area is detected from a medical image using various lesion area detecting algorithms, a group of candidate lesion areas may be generated from the detected lesion area by performing segmentation on the detected original lesion area in 320.

In response to the generation of the group of candidate lesion areas, detailed analytical information including feature information, class information and diagnostic result information may be generated with respect to each of the candidate lesion areas. For example, the class information and the diagnostic result information may be generated by analyzing the feature information on each of the candidate lesion areas using various analysis algorithms.

Once the group of candidate lesion areas is generated, one or more candidate lesion areas are selected from among the group of candidate lesion areas in 330. For example, the one or more candidate lesion areas are selected from the group of candidate lesion areas to be displayed on an interface 10. An example of such an interface 10 is illustrated in FIG. 2. The selection regarding which of the candidate lesion areas are displayed is performed based on priorities relative to the group of candidate lesion areas. The priorities may be determined according to a predetermined criterion. For example, the predetermined criterion may be a probability of a user selecting a candidate lesion area from among the group of candidate lesion areas.

Next, the one or more selected candidate lesion areas and brief analytical information about each of the one or more selected candidate lesion area may be arranged in the interface according to the predetermined criterion in 340. In this example, the brief analytical information may include at least one of feature information, class information and diagnostic result information among detailed analytical information generated with respect to each of the one or more selected candidate lesion areas. The predetermined criterion may include at least one of priority information calculated with respect to the one or more candidate lesion areas, the class information about each of the one or more candidate lesion areas, and a combination of the priority information and the class information.

As described above with reference to FIGS. 2 and 4, a candidate lesion area having the highest priority may be arranged at the center of the first region 20 based on priorities among the one or more candidate lesion areas 21. Other candidate lesion areas 21 may be arranged on the left or the right of the candidate lesion area displayed in the center by alternating between the left side and the right side in descending order of the priorities. In another example, based on the priorities, the one or more candidate lesion areas 21 with different sizes may be displayed on the first region 20, or frames of different sizes may be used to display the one or more candidate lesion areas in the first region 20. In another example, one or more different colors may be used for boundaries of the one or more candidate lesion areas 21 or for frames in which the one or more candidate lesion areas 21 and brief analytical information thereof are to be displayed.

In another example, the one or more candidate lesion areas 21 may be arranged based on the class information of the candidate lesion areas in the first region 20. In yet another example, based on the class levels, one or more different colors may be used for boundaries of the one or more candidate lesion areas 21 or for frames in which the one or more candidate lesion areas 21 and brief analytical information thereof are to be displayed.

Next, as illustrated in FIG. 4, in the event that a user selects one of the candidate lesion areas 21 displayed on the first region 20, detailed analytical information about the user selected candidate lesion area 21 may be displayed on the second region 30 of the interface in 350. Feature information contained in the detailed analytical information displayed on the second region 30 may include at least some feature categories. The feature categories to be displayed are selected from among one or more feature categories which are extracted with respect to the selected candidate lesion area 21 based on priorities calculated according to a predetermined criterion. The feature information may also include at least one feature corresponding to each of the feature categories to be displayed.

In the event that a user selects one of the feature categories displayed on the second region 30 for modification, at least some features out of features corresponding to the selected feature category may be provided to a user in 360. As described with reference to FIG. 4, in the event that a user selects a feature such as "shape" placed on top of other features displayed on the second area 30 for modification, features to be provided to a user, that is, features having the top three highest priorities, are selected and displayed on a pop-up window in a predetermined region fv of the interface 10.

In the event that the user selects one of the features displayed in the interface 10 as a way of requesting a modification, the selected feature is received and stored as a final diagnostic result.

Various examples of apparatus and methods are described above. In an example, an apparatus may support computer-aided diagnosis. The apparatus may include an analyzing unit configured to detect an original lesion area by analyzing a medical image, and generate a group of candidate lesion areas with respect to the detected original lesion area. The apparatus may include an interface unit configured to arrange one or more candidate lesion areas selected from among the group of candidate lesion areas and brief analytical information about each of the one or more selected candidate lesion areas in a first region of an interface according to a predetermined criterion. The predetermined criterion may include at least one of priority information and class information about each of the one or more selected candidate lesion areas and a combination of the priority information and the class information.

The interface unit may arrange a candidate lesion area having a higher priority to be closer to a center of the first region of the interface, compared to another candidate lesion area having a relatively lower priority. The interface unit may arrange candidate lesion areas with different sizes in the first region based on the priorities. The interface unit may arrange the candidate lesion areas based on the class information thereof in the first region. The interface unit may arrange the one or more selected candidate lesion areas with boundaries or frames with different colors in the first region based on class information of the candidate lesion areas.

The apparatus may further include a processing unit configured to calculate priorities relative to the group of candidate lesion areas according to the predetermined criterion, and select one or more candidate lesion areas from among the group of candidate lesion areas based on the priorities. The predetermined criterion may be a probability of a user selecting a candidate lesion area from among the group of candidate lesion areas.

In response to a user selecting one of the candidate lesion areas arranged in the first region, the interface unit may display detailed analytical information about the selected candidate lesion area in a second region of the interface. The detailed analytical information may include at least one of feature information, which includes one or more feature categories and one or more features corresponding each of the one or more feature categories, class information and diagnostic result information. The interface unit may display in the second region at least some feature categories, selected based on priorities among feature categories relating to the selected candidate lesion area, and at least one feature selected based on priorities among features corresponding to each of the at least some feature categories. In the event that a user selects one of the at least some feature categories displayed on the second region, the interface unit may display at least some features selected based on priorities among features corresponding to the selected feature category.

In another example, a method of diagnosis is described. The method may support a computer-aided diagnosis. The method may involve detecting an original lesion area by analyzing a medical image; generating a group of candidate lesion areas with respect to the detected original lesion area; and arranging one or more candidate lesion areas selected from among the group of candidate lesion areas and brief analytical information about each of the one or more selected candidate lesion areas in a first region of an interface according to a predetermined criterion. The predetermined criterion may include at least one of priority information and class information about each of the one or more selected candidate lesion areas and a combination of the priority information and the class information.

The arranging of the one or more selected candidate lesion areas may include arranging a candidate lesion area having a higher priority to be closer to a center of the first region, compared to another candidate lesion area having a relatively lower priority. The arranging of the one or more selected candidate lesion areas in the first region may include arranging the one or more candidate lesion areas of different sizes in the first region based on priorities among the one or more selected candidate lesion areas. The arranging of the one or more selected candidate lesion areas in the first region may include arranging the one or more selected candidate lesion areas based on the class information thereof in the first region. The arranging of the one or more selected candidate lesion areas in the first region may include arranging the one or more selected candidate lesion areas with different-colored boundaries or frames in the first region according to class levels thereof.

The method may further include calculating priorities relative to the group of candidate lesion areas and selecting one or more candidate lesion areas from among the group of candidate lesion areas according to the predetermined criterion. The predetermined criterion may be a probability of a user selecting a candidate lesion area from among the group of candidate lesion areas. The method may further include, if a user selects one of the one or more selected candidate lesion areas arranged in the first region, displaying detailed analytical information about the selected candidate lesion area in a second region of the interface. The detailed analytical information may include at least one of feature information, which comprises one or more feature categories and one or more features corresponding each of the one or more feature categories, class information and diagnostic result information.

The displaying of the detailed analytical information in the second region may include displaying at least some feature categories selected based on priorities among the one or more feature categories relating to the selected candidate lesion area, and at least one feature selected based on priorities among features corresponding each of the at least some feature categories. The method may further include, in response to a user selecting one of the at least some feature categories displayed on the second region, displaying at least some features selected based on priorities among features corresponding to the selected feature category.

Various examples of methods and units described above may be implemented in part, with computer-readable codes. The computer readable codes may be stored in a non-transitory computer-readable recording medium. The computer-readable recording medium includes all types of recording devices which stores computer-system readable data.

Examples of non-transitory computer-readable recording medium includes a Read Only Memory (ROM), a Random Access Memory (RAM), a CD-ROM, a magnetic tape, a floppy disk, flash memory, and an optical data storage device, and the computer readable recording medium may be realized in a carrier wave form (for example, transition via the Internet). In addition, the computer-readable recording medium is distributed in a computer system connected via a network so that computer-readable codes are stored and executed in a distributed manner.

Various units as described above may be implemented using hardware components and software components. For example, the units may include a processing device, a display unit, a touch screen, a microprocessor, a memory, a data storage unit, radio signal transmitter, internet server, and the like. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller, and a processor may be shared between two or more units.

The software may include a computer program, a piece of code, an instruction, or some combination thereof, for independently or collectively instructing or configuring the processing device to operate as desired. Programs, codes, and code segments for accomplishing the examples disclosed herein can be easily implemented by programmers skilled in the art to which the examples pertain based on and using the flow diagrams and block diagrams of the figures and their corresponding descriptions as provided above.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus, comprising:
a memory configured to store instructions;
a display; and
at least one processor, electrically coupled to the memory and the display, configured to execute the stored instructions to:
identify, based on detecting a lesion area within a medical image, a first reference lesion area with a first priority and a second reference lesion area with a second priority that is higher than the first priority from data that is pre-stored in the apparatus and has been obtained independently from the medical image, the first reference lesion area and the second reference lesion area associated with the detected lesion area, and display the first reference lesion area included in a first frame and the second reference lesion area included in a second frame within a first region of an interface and the detected lesion area within a second region of the interface, wherein the displayed second frame is highlighted relative to the displayed first frame.

2. The apparatus of claim 1, wherein the second frame is highlighted by displaying at least a portion of the second frame in a second color that is different than a first color of the display of the first frame.

3. The apparatus of claim 2, wherein the second color is brighter than, darker than, or different color than the first color.

4. The apparatus of claim 1, wherein the first reference lesion area included in the first frame and the second reference lesion area included in the second frame have different degrees of darkness.

5. The apparatus of claim 1,
wherein the at least one processor is further configured to execute the stored instructions to display, based on class information, the first reference lesion area included in the first frame and the second reference lesion area included in the second frame, and
wherein the class information is used for indicating a degree of benignancy or malignancy of the first reference lesion area and the second reference lesion area.

6. The apparatus of claim 1, wherein the at least one processor is further configured to execute the stored instructions to display, within the first region of the interface, first information on a shape of the first reference lesion area and second information on a shape of the second reference lesion area.

7. The apparatus of claim 1, wherein the at least one processor is further configured to execute the stored instructions to:
display, in response to detecting an input for selecting a reference lesion area from among the first reference lesion area and the second reference lesion area, detailed information on the selected reference lesion area within a third region of the interface.

8. The apparatus of claim 7, wherein the detailed information comprises feature information comprising one or more feature categories on the selected reference lesion area, class information regarding the selected reference lesion area, or diagnostic result information regarding the selected reference lesion area.

9. The apparatus of claim 8, wherein the feature information further comprises one or more features corresponding to the one or more feature categories.

10. The apparatus of claim 9,
wherein the one or more feature categories comprise one or more of a shape, a margin, an echo pattern, an orientation, or a boundary of the selected reference lesion area, and
wherein the one or more features comprise one or more of an irregular shape, a round shape, or an oval shape.

11. A method of displaying in an apparatus, the method comprising:
identifying, based on detecting a lesion area within a medical image, a first reference lesion area with a first priority and a second reference lesion area with a second priority that is higher than the first priority from data that is pre-stored in the apparatus and has been obtained independently from the medical image, the first reference lesion area and the second reference lesion area associated with the detected lesion area; and displaying the first reference lesion area included in a first frame and the second reference lesion area included in a second frame within a first region of an interface and the detected lesion area within a second region of the interface, wherein the displayed second frame is highlighted relative to the displayed first frame.

12. The method of claim 11, wherein the second frame is highlighted by displaying at least a portion of the second frame in a second color that is different than a first color of the display of the first frame.

13. The method of claim 11, wherein the second color is brighter than, darker than, or different color than the first color.

14. The method of claim 11, wherein the first reference lesion area included in the first frame and the second reference lesion area included in the second frame have different degrees of darkness.

15. The method of claim 11,
wherein the displaying of the first reference lesion area and the second reference lesion area comprises displaying, based on class information, the first reference lesion area included in the first frame and the second reference lesion area included in the second frame, and
wherein the class information is used for indicating a degree of benignancy or malignancy of the first reference lesion area and the second reference lesion area.

16. The method of claim 11, further comprising:
displaying, within the first region of the interface, first information on a shape of the first reference lesion area and second information on a shape of the second reference lesion area.

17. The method of claim 11, further comprising:
displaying, in response to detecting an input for selecting a reference lesion area from among the first reference lesion area and the second reference lesion area, detailed information on the selected reference lesion area within a third region of the interface.

18. The method of claim 17, wherein the detailed information comprises feature information comprising one or more feature categories on the selected reference lesion area, class information regarding the selected reference lesion area, or diagnostic result information regarding the selected reference lesion area.

19. The method of claim 18, wherein the feature information further comprises one or more features corresponding to the one or more feature categories.

20. A computer program product comprising a non-transitory computer readable storage medium having a computer readable program stored therein, wherein the computer readable program, when executed on at least one processor, configures the at least one processor to:
identify, based on detecting a lesion area within a medical image, a first reference lesion area with a first priority and a second reference lesion area with a second priority that is higher than the first priority from data that is pre-stored and has been obtained independently from the medical image, the first reference lesion area and the second reference lesion area associated with the detected lesion area; and display the first reference lesion area included in a first frame and the second reference lesion area included in a second frame within a first region of an interface and the detected lesion area within a second region of the interface,
wherein the displayed second frame is highlighted relative to the displayed first frame.

\* \* \* \* \*